United States Patent [19]

Glenn

[11] 4,017,972
[45] Apr. 19, 1977

[54] DOWEL PIN POSITIONER

[76] Inventor: Edward C. Glenn, 1455 NE. 55th St., Fort Lauderdale, Fla. 33334

[22] Filed: July 7, 1975

[21] Appl. No.: 593,280

[52] U.S. Cl. .................................................. 32/11
[51] Int. Cl.² ......................................... A61C 13/00
[58] Field of Search ............................. 32/11, 40 R

[56] References Cited

UNITED STATES PATENTS

| | | | |
|---|---|---|---|
| 1,722,306 | 7/1929 | Murray | 32/32 |
| 2,608,762 | 9/1952 | Fox | 32/32 |
| 3,650,032 | 3/1972 | Kestler | 32/11 |

Primary Examiner—Robert Peshock
Attorney, Agent, or Firm—Malin & Haley

[57] ABSTRACT

A device which provides for the positioning, alignment, and holding of dowel pins utilized in the construction of positive molds of a patient's teeth with removeable dies for dental prosthetic and restoration devices, including inlays, crowns, fixed and removeable bridges and precision attachments. The device includes a supporting rack, arch-shaped (as a row of teeth) and constructed of magnetized material, which receives a plurality of magnetizable dowel pin holders which are moveably positionable but firmly retained against the supporting rack. In one embodiment, the dowel pin holders are T-shaped and include a vertically adjustable tensioning means. The dowel pin holders when coupled to the supporting rack are positionable horizontally and vertically above a mold or impression which is received on a separate tray. The device allows for the positioning and holding of dowel pins in a manually arranged, three dimensional array, alleviating the use of complicated and complex connectors as found in the prior art.

2 Claims, 3 Drawing Figures

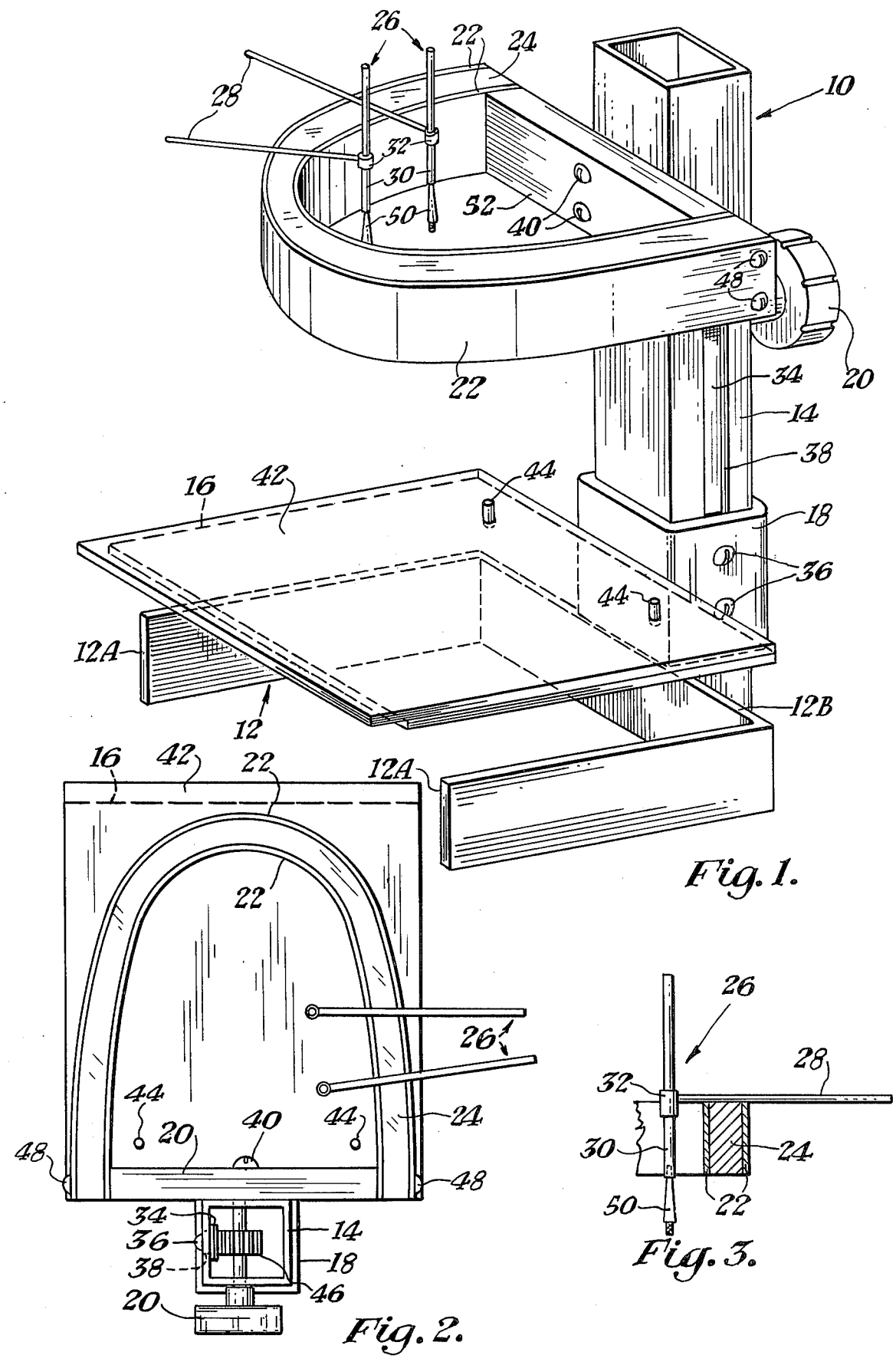

DOWEL PIN POSITIONER

BACKGROUND OF THE INVENTION

This invention relates generally to a device for positioning and supporting a plurality of dowel pins which are utilized in the construction of dental prosthetic devices, and specifically to an improved dowel pin positioner which allows for rapid and non-complex dowel pin positioning. The use of a device for positioning and holding dowel pins which are used in the making of removeable tooth dies are known in the prior art. An example of a device used is the device shown in U.S. Pat. No. 2,669,780, issued to Mann which shows the use of C clamps to hold the dowel pins disposed about a supporting rack, the pins being manually fastened by screws to the rack surface. One of the problems with a device such as this is that the C clamps are bulky and are cumbersome when positioning dowel pins over impression areas which require dowel pins be placed close together. The size of the C clamps prevents the use of a maximum number of dowel pins, which could be as many as 16.

The instant invention overcomes the problems of the prior art by providing a dowel pin positioner which utilizes magnetized material on a dowel pin holder supporting rack in conjunction with metal dowel pin holders which are magnetizable to allow the dowel pin holders to be positioned and magnetically connected to the arch-shaped supporting rack. By reducing the dowel pin holder connector complexity and size, the instant invention can employ up to 16 dowel pin holders at one time.

BRIEF DESCRIPTION OF THE INVENTION

A device for positioning and retaining a plurality of dowel pins utilized for the construction of dental prosthetic and restoration devices comprising a base, a rigid, vertically disposed support member connected at one end to said base, a moveable tray table coupled to said vertical support member, said moveable tray table including a means for manually moving said tray table vertically relative to said vertical support member, a removeable tray connectable to said tray table, a dowel pin holder support rack coupled to the upper end of said vertical support member, said rack including a horseshoe-shaped bar of magnetized material for receiving and attaching a plurality of dowel pin holders thereto. The dowel pin holders consist of a magnetizable material and are substantially T-shaped and include a dowel pin mandrel tube which is moveably connected to a flat pin hold bar by a tension tube. The flat pin holder bar is shaped and sized to be magnetically attached horizontally to the upper portion of the horseshoe-shaped magnetizable bar.

The base may include a pair of parallel legs connected to a cross bar.

To operate the device, an impression of the teeth and arch of conventional impression material is positioned on the tray with putty-like material (mortite), the tray being removeable from the tray table. The dowel pins are positioned in the dowel pin mandrel tube in mortite or carding wax such that the dowel pin is attached to the dowel pin holder. The tray, with the elastic mold, is then elevated to the desired position by movement of the tray table. The dowel pin holders are horizontally positioned over selected impression cavity areas. The mandrel tube of the dowel pin holder is adjustable vertically relative to the flat-surfaced pin holder to allow manual vertical movement of each dowel pin within the elastic material impression or mold on the tray such that the dowel pins will be disposed inside the mold at the proper elevational level. The adjustment of the dowel pin position within the mold cavity is accomplished prior to any pouring of the die material. After the vertical adjustment of the dowel pins is accomplished, the tray table is then lowered and the tray with the impression material or mold is removed from the tray table and is filled with die material. The tray with the impression or mold and the die material is then mounted again on the tray table using lugs which allow the tray table to be retained in the same relative position as it was prior to removal. The table is raised to the position where the dowel pins are received into the die material in the impression at the proper depth. After the die material has hardened, the dowel pin holders are detached from the dowel pins.

It is an object of this invention to provide an improved dowel pin positioning and retaining device, utilized in the construction of dental prosthetic appliances.

It is another object of this invention to provide a dowel pin holder supporting device which allows for the use of a plurality of dowel pins which may easily and quickly be manually adjusted to the proper position within the impression device.

And yet still another object of this invention is to reduce the complexity of the connection of the dowel pin holders to the supporting device as utilized in a dowel pin parallator by the employment of a magnetizable material in conjunction with magnetizable dowel pin holders which may be readily connected thereto.

But yet still another object of this invention is to provide a dowel pin positioner which allow positioning of from one to sixteen dowel pins, accurately and which may be operated by untrained or semi-skilled personnel.

In accordance with these and other objects which will be apparent hereinafter, the instant invention will now be described with particular reference to the accompanying drawings.

BRIEF DESCRIPTION OF THE DRAWINGS

FIG. 1 shows a dowel pin positioning device in perspective constructed in accordance with the instant invention.

FIG. 2 shows a top plan view of the instant invention including a pair of dowel pin holders.

FIG. 3 shows a side elevational view of a dowel pin holder attached to a cross-sectional view of the dowel pin holder supporting rack.

PREFERRED EMBODIMENT OF THE INVENTION

Referring now to the drawings and especially FIG. 1, the instant invention is shown generally at 10 comprising a base 12 which includes a pair of rigid, parallel legs 12A joined together by a cross-section member 12B which is fixed to rigid, hollow vertical support member 14 by a connector (not shown). A horizontally disposed tray table 16 is rigidly fixed to slip ring 18 which is mounted about the vertical support tube 14. Connected to the upper surface of the tray table 16 are a pair of guides 44 which are lugs mounted to the upper surface of tray table 16. The guides 44 act as alignment aids for removeable tray 42, which is mountable on the upper surface of the tray table 16, the removeable tray 42 being used to receive the mold or molded impression material which is discussed further below. The tray table actuating knob 20 is connected to the spur gear 46 (FIG. 2) which engages a gear rack 34 disposed within the vertical support member 14 and which is connected to slip ring 18 by screws 36 which are received through slot 38 in the vertical support member 14. Manual rotation of the knob 20 moves the tray table 16 vertically (up or down, dependent upon the direction of rotation). Attached by screws 40 to one side adjacent the upper end of vertical support member 14 is an arm 52 which is connected to U-shaped or horseshoe-shaped flexible strips of magnetic material 24 having metal strips 22 disposed on its vertical sides.

The dowel pin holder supporting rack is curved in an arch shaped similar to a row of teeth. FIG. 2 shows the dowel pin holder supporting rack comprised of curved metal strips 22 disposed on each side of arch-shaped magnetic bar 24, with the strips from the bar being attached by screws 48 to the arm 52 which is connected by screws 40 to one side of the rigid vertical support member 14. Disposed on the top surface of the supporting rack on top of the metal strips 22 are a pair of dowel pin holders 26 with attached dowel pins 50 (FIG. 3), illustrating the manner in which the dowel pin holders are positioned. Gear rack 34 is connected by screws 36 through slot 38 in the vertical support member 14 to slip ring 18, rigidly fixed to the tray table 16. Rotation of knob 20 connected to gear 46 (which is intermeshed with rack 34) causes the rack to move either upwardly or downwardly, thus moving the slip ring and the tray table.

FIG. 3 shows a dowel pin holder 26 which is substantially T-shaped and formed with flat metal arm 28 having a tensioning tube 32 which receives and is coupled to the dowel pin mandrel 30. A conventional dowel pin 50 is connected to the mandrel 30. In operation, each dowel pin holder 26 including flat holder bar 28 is disposed on the upper surface of rack 24, resting upon the upper edges of metal strips 22. The tensioning tube 32 provides a frictional clamp for adjusting the mandrel vertically (and dowel pin 50) relative to the top of rack 24. The vertical adjustment of the dowel pin holder mandrels is done with the mold or impression cavities empty prior to the pouring of the die material.

To operate the instant invention, an impression is placed on removeable tray 42 and elevated by knob 20 which actuates the spur gear 46 (FIG. 2) to the gear rack 34 and slip ring 18, causing the impression to be moved upward in a vertical direction. The dowel pin holders with the dowel pins attached are placed along the upper surface edges of metal strips 22 and the dowel pin holders 26 including the pin mandrel tubes 30 adjusted to position the dowel pins 50 in the desired vertical and horizontal position within the empty impression. The magnetic force firmly retains each dowel pin holder wherever positioned, while still allowing for manual horizontal movement when necessary. After all the pins are correctly positioned within the empty impression, the tray table 16 and impression are lowered and the tray 42 removed. Die material is poured into the impression mold and the tray 42 reattached to table 16 being returned to the same relative position by guides 44. The impression with the die material is then repositioned relative to the dowel pins. After the material has been hardened sufficiently, the dowel pin holders may then be separated from the dowel pins themselves.

The instant invention has been shown and described herein in what is considered to be the most practical and preferred embodiment. It is recognized, however, that departures may be made therefrom within the scope of the invention and that obvious modifications will occur to a person skilled in the art.

What I claim is:

1. A dowel pin positioning device for positioning dowel pins utilized in the construction of dental prosthetic appliances from impression devices comprising:

a rigid, hollow vertical support shaft, said shaft having a vertical slot;

a base member connected to one end of said rigid, vertical support shaft, said base member supporting said shaft in a vertical position;

a rigid, horizontally disposed dowel pin holder supporting member rigidly connected to said vertical support shaft near the upper free end of said support shaft, said dowel pin holder support member including a horseshoe shaped magnet and a connecting bar disposed between the free ends of said horseshoe magnet, said connecting bar rigidly fixed to said vertical support member;

a rigid platform;

a slip ring connected around the outer circumference of said vertical shaft, said slip ring rigidly fixed to said rigid platform, said platform being horizontally disposed, a gear rack connected within said hollow interior of said support shaft and connected to said slip ring;

a fastening means connected to said slip ring and said gear rack through said vertical shaft slot;

a ring gear rotatably connected within said hollow vertical shaft and engaged with said gear rack;

means for rotating said ring gear connected to said ring gear and mounted on said vertical shaft;

a removeable tray mountable on said rigid, planar platform, said tray adapted to receive impressionable materials;

a means for aligning said removeable tray with said rigid platform when said removeable tray is mounted on said platform; and at least one dowel pin holder magnetically attachable to said horseshoe magnet upper surface, said dowel pin holder including a flat, magnetizable bar, said bar having a friction clip disposed at one end, and a dowel pin receiving mandrel frictionally moveable, disposed in said clip, said mandrel being frictionally adjustable in position relative to said clip.

2. A dowel pin positioning device as in claim 1, including:

a pair of metal strips, each of said strips being disposed on opposite sides of said horseshoe magnet, said strips being disposed vertically such that one of said strips is mounted on the outside surface of said horseshoe magnet and the other of said strips is mounted on the inside of the horseshoe portion of the magnet, the upper edges of the surface being aligned to engage said flat dowel pin holder bar.

* * * * *